United States Patent [19]
Tsukuno et al.

[11] Patent Number: 5,922,893
[45] Date of Patent: Jul. 13, 1999

[54] METHOD FOR PREPARING MONOSILANES FROM A HIGH-BOILING FRACTION FORMED AS BY-PRODUCTS IN THE DIRECT SYNTHESIS OF METHYLCHLOROSILANES

[75] Inventors: Akihito Tsukuno; Yukinori Satoh; Masao Maruyama, all of Annaka; Kesaji Harada, Chiyoda-ku; Shoichi Tanaka, Usui-gun; Masaaki Furuya, Annaka, all of Japan

[73] Assignee: Shin-Etsu Chemical Co., Ltd., Japan

[21] Appl. No.: 09/031,545

[22] Filed: Feb. 27, 1998

[30] Foreign Application Priority Data

Feb. 28, 1997 [JP] Japan .................................... 9-062383

[51] Int. Cl.$^6$ ........................................................ C02F 7/08
[52] U.S. Cl. ............................................ 556/468; 556/467
[58] Field of Search ...................................... 556/467, 468

[56] References Cited

U.S. PATENT DOCUMENTS

| | | |
|---|---|---|
| 2,709,176 | 5/1955 | Bluestein et al. . |
| 3,432,537 | 3/1969 | Guinet et al. . |
| 3,878,234 | 4/1975 | Atwell et al. ............................ 556/468 |
| 4,059,607 | 11/1977 | Reedy et al. ............................. 556/468 |
| 5,288,892 | 2/1994 | Pachaly et al. ..................... 556/468 X |
| 5,321,147 | 6/1994 | Chadwick et al. ................. 556/468 X |
| 5,502,230 | 3/1996 | Mautner et al. ........................ 556/468 |
| 5,627,297 | 5/1997 | Gilbert et al. ........................... 556/467 |
| 5,627,298 | 5/1997 | Freeburne et al. ..................... 556/467 |
| 5,629,438 | 5/1997 | Freeburne et al. ..................... 556/467 |

FOREIGN PATENT DOCUMENTS

| B 6869 | 8/1957 | Japan . |
|---|---|---|
| B 8458 | 7/1968 | Japan . |

*Primary Examiner*—Paul F. Shaver
*Attorney, Agent, or Firm*—Millen, White, Zelano, & Branigan, P.C.

[57] ABSTRACT

The direct synthesis of methylchlorosilanes to react metallic silicon with methyl chloride in the presence of a copper catalyst yields a high-boiling fraction of methylchlorodisilanes as by-products. The invention provides a method for preparing monosilanes from the high-boiling fraction by reacting it with hydrogen chloride in the presence of an amine or amide catalyst. The reaction is effected under the condition that the amount of iron, aluminum, zinc, tin and compounds thereof present in the reaction system is less than the equimolar amount with respect to the catalyst. This increases the conversion of disilanes into monosilanes.

10 Claims, No Drawings

METHOD FOR PREPARING MONOSILANES FROM A HIGH-BOILING FRACTION FORMED AS BY-PRODUCTS IN THE DIRECT SYNTHESIS OF METHYLCHLOROSILANES

BACKGROUND OF THE INVENTION

1. Field of the Invention

This invention relates to a method for preparing monosilanes from a high-boiling fraction of methylchlorodisilanes formed as by-products in the direct synthesis of methylchlorosilanes.

2. Prior Art

It is well known to produce methylchlorosilanes by reacting metallic silicon and methyl chloride as reactants in the presence of copper catalysts. There are produced monosilanes such as dimethyldichlorosilane, trimethylchlorosilane, methyltrichlorosilane, and methylhydrogen-dichlorosilane. This process is often referred to as the direct synthesis of methylchlorosilanes. The direct synthesis process is disclosed in Rochow, U.S. Pat. Nos. 2,380,995 and 2,488,487. It is a predominant industrial process for the manufacture of monosilanes.

A variety of modified silanes, silicon-containing compounds and silicone polymers are derived from these monosilanes utilizing their reactive sites. These derivatives now find use in electric, cosmetic and other industries depending on their properties.

The direct synthesis of methylchlorosilanes yields not only the desired monosilanes mentioned above, but also a high-boiling fraction of methylchlorodisilanes of the general formula (1):

$$(CH_3)_a Si_2 Cl_{6-a} \qquad (1)$$

wherein letter a is an integer of 2 to 6.

In the industrial scale synthesis of methylchlorosilanes in the state of the art, this high-boiling fraction usually accounts for about 10% of a crude product. It is economically and ecologically important to convert the high-boiling fraction into valuable monosilanes for reducing waste residues.

One well-known method for converting the high-boiling fraction into monosilanes is by reacting the high-boiling fraction with hydrogen chloride. The method for converting the high-boiling fraction into monosilanes through reaction with hydrogen chloride is disclosed in JP-B 6869/1957, 8458/1968, French Patent No. 1119915, W. Noll, Chemie und Technologie der Silicone, 2nd Ed., 1968, Chap. 2.2.8, and Pachaly, U.S. Pat. No. 5,288,892. These publications describe:

(i) that methylchlorodisilanes are converted into monosilanes by cleaving Si—Si bonds in methylchlorodisilanes using a tertiary amine and halogenic acid;

(ii) that reaction is carried out in an evaporator with an attached column;

(iii) that by-products are separated into disilanes cleavable with hydrogen chloride and noncleavable disilanes, and the cleavable disilanes are subject to reaction; and (iv) that this separation is continuously carried out.

In these prior art methods, however, monosilanes are recovered in low yields because the conversion of high-boiling residues into monosilanes is insufficient.

After the high-boiling fraction is reacted with hydrogen chloride, there is left unreacted hydrogen chloride. One common treatment of the unreacted hydrogen chloride is scrubbing with water. This treatment has the drawback that the effective utilization of scrubbed hydrogen chloride generally requires a large size of equipment and enormous energy consumption. The scrubbing treatment is also economically disadvantageous in that it adds to the load for the disposal of plant waste water containing hydrogen chloride.

SUMMARY OF THE INVENTION

An object of the invention is to provide a novel and improved method for preparing monosilanes from a high-boiling fraction of methylchlorodisilanes formed as by-products in the direct synthesis of methylchlorosilanes, featuring a high degree of conversion from the high-boiling fraction to monosilanes and an economical advantage.

The direct synthesis of methylchlorosilanes by reacting metallic silicon with methyl chloride in the presence of a copper catalyst yields as by-products a high-boiling fraction consisting essentially of methylchlorodisilanes of the general formula (1):

$$(CH_3)_a Si_2 Cl_{6-a} \qquad (1)$$

wherein letter a is an integer of 2 to 6. By reacting the high-boiling fraction with hydrogen chloride in the presence of an amine or amide catalyst, monosilanes are obtained from the high-boiling fraction. We have found that monosilanes can be produced from the high-boiling fraction in an industrially advantageous manner by effecting the reaction of the high-boiling fraction with hydrogen chloride under the condition that the amount of impurities which can deactivate the amine or amide catalyst and which are present in the high-boiling fraction and the reaction system is less than the equimolar amount for the catalyst.

Therefore, the present invention provides a method for preparing monosilanes from a high-boiling fraction formed as by-products in the direct synthesis of methylchlorosilanes by reacting metallic silicon with methyl chloride in the presence of a copper catalyst, the high-boiling fraction consisting essentially of methylchlorodisilanes of the general formula (1):

$$(CH_3)_a Si_2 Cl_{6-a} \qquad (1)$$

wherein letter a is an integer of 2 to 6. According to the invention, the high-boiling fraction is reacted with hydrogen chloride in the presence of an amine or amide catalyst and under the condition that the amount of iron, aluminum, zinc, tin and compounds thereof present in the reaction system is less than the equimolar amount for the catalyst.

In one preferred embodiment, unreacted hydrogen chloride is absorbed in a silane, and the hydrogen chloride-absorbed silane is recycled to the reaction system of the high-boiling fraction and hydrogen chloride.

More particularly, the high-boiling fraction of methylchlorodisilanes of formula (1) is formed as by-products in the direct synthesis of methylchlorosilanes. The direct synthesis of methylchlorosilanes is industrially carried out in a heterogeneous reaction system using metallic silicon powder and methyl chloride in a fluidized bed reactor. The metallic silicon powder generally contains iron, aluminum, calcium and other impurities. In addition, copper or copper compounds are used as a catalyst. The impurities in the metallic silicon powder and the material introduced into the fluidized bed reactor as the catalyst are carried over in more or less amounts, along with a crude product containing the high-boiling fraction. Consequently, the high-boiling fraction contains not only cleavable methylchlorodisilanes, but also silicon-containing solid matter, dissolvable or undissolvable compounds of copper and aluminum and the like as impurities. The concentration of such impurities in the high-boiling fraction is uncertain because it depends on the concentration of impurities in the metallic silicon powder, the type and amount of the catalyst used, and the construction and capacity of the fluidized bed reactor and attachments. Where a reactor made of iron is used, compounds of iron etc. form by corrosion and other chemical changes, also constituting impurities in the reaction system.

On the other hand, the reaction of methylchlorodisilanes with hydrogen chloride is generally carried out by introducing hydrogen chloride gas into the methylchlorodisilanes. Amines and amides are used herein as a catalyst. The cleavage of silicon-to-silicon bonds in the methylchlorodisilanes takes place primarily as a result of catalysis of a tertiary amine and secondarily as a result of the co-presence of hydrogen chloride and tertiary amine.

Also, the reaction of methylchlorodisilanes with hydrogen chloride is generally carried out in a continuous or semi-continuous manner using an evaporator with an attached column as the reactor. With respect to the continuation of reaction, it is disclosed in U.S. Pat. No. 5,288,892 that reaction can be continuously carried out by continuously removing from the reaction mixture all the compounds which are more volatile than the cleavable methylchlorodisilanes, and that if these compounds are not continuously removed from the reactor, the noncleavable components in the methylchlorodisilanes build up in the reaction mixture and necessitate regular evacuation of the contents from the reactor.

However, with respect to the reaction of methylchlorodisilanes with hydrogen chloride, no prior art references discuss the influence on the reaction of impurities in the disilanes and the reaction system. This means that the prior art paid no attention to the impurities in the methylchlorodisilanes (high-boiling fraction) formed as by-products in the direct synthesis of methylchlorosilanes and in the reaction system. Regarding the reaction of methylchlorodisilanes with hydrogen chloride, we have found that dissolvable or undissolvable impurities, especially iron, zinc, tin, aluminum and compounds thereof, which are contained in the starting methylchlorodisilanes and present in the reaction system, become catalyst poisons in the reaction, that is, obstruct the progress of reaction of methylchlorodisilanes with hydrogen chloride to form monosilanes. We have further found that by previously removing these impurities from the starting methylchlorodisilanes and using a properly lined reactor instead of an iron reactor, the amount of the catalyst necessary for the reaction can be reduced to a minimum necessary amount to accomplish the desired reaction rate, and when the reaction is carried out using the same amount of catalyst, a long-term continuous run becomes possible without inviting a reduction of the life of reaction, that is, a lowering of reactivity.

According to the invention, since the high-boiling fraction is subject to reaction after the content of impurities in the high-boiling fraction is reduced and after a system (including a reactor) is tailored to prevent impurities from being extracted therefrom to the reaction medium, it becomes possible to prevent the deactivation of the catalyst. As a result, the batch life is improved, thereby reducing the loss time of the process and the loss of silanes. Since the catalyst is not deactivated, the expense for the catalyst is minimized. Since the amount of catalyst can be reduced, the concentration of catalyst in the reactor is also reduced. This restrains the catalyst used from inducing any side reactions, for example, further decomposition of methylhydrogendichlorosilane formed from cleavage, thereby contributing to an improvement in the yield of monosilanes. The invention is thus of great worth from the industrial standpoint.

The reason why the reduction of the impurities is effective is not well understood. Where an impurity in methylchlorodisilanes is aluminum chloride which is a Lewis acid, for example, the reduction of the impurity is effective for minimizing the possibility that this aluminum chloride will react with the catalyst, for example, a tertiary amine, to deprive the catalyst of its catalytic ability to cleave silicon-to-silicon bonds.

Regarding the reaction of the high-boiling fraction (methylchlorodisilanes) with hydrogen chloride, we have further found that an unreacted portion of the hydrogen chloride used in the reaction can be readily recovered by absorbing the unreacted hydrogen chloride in silanes such as dimethyldichlorosilane and methyltrichlorosilane and recycling the silanes containing hydrogen chloride to the reactor where the hydrogen chloride is subject to reaction again.

The procedure of absorbing the unreacted hydrogen chloride in silanes, recycling the silanes to the reactor, and subjecting the hydrogen chloride to reaction again has the advantage that since silanes are used as an absorbent medium, the silane liquid having hydrogen chloride absorbed therein can be directly fed back to the reactor without a need for separation or other extra operation. The number of units necessary for hydrogen chloride recovery is minimized. As a result, the percent utilization of the hydrogen chloride gas charge is increased. This makes the preparation of monosilanes economically more advantageous. Additionally, the amount of unreacted hydrogen chloride gas in the exhaust gases is reduced, which has the advantage of reducing the investment and running costs of scrubbing equipment which is commonly used for the disposal of hydrogen chloride gas in the prior art. The invention is of great industrial worth in this respect, too.

DESCRIPTION OF THE PREFERRED EMBODIMENTS

In the direct synthesis of methylchlorosilanes by reacting metallic silicon with methyl chloride in the presence of a copper catalyst, there is formed as by-products a high-boiling fraction consisting essentially of methylchlorodisilanes of the general formula (1):

$$(CH_3)_a Si_2 Cl_{6-a} \tag{1}$$

wherein letter a is an integer of 2 to 6. The present invention provides a method for preparing monosilanes from this high-boiling fraction by reacting it with hydrogen chloride.

The direct synthesis of methylchlorosilanes may be carried out by well-known techniques. The separation of methylchlorodisilane by-products from the methylchlorosilane reaction product may also be carried out by well-known techniques.

According to the invention, the thus separated methylchlorodisilanes are reacted with hydrogen chloride in the presence of catalysts. The catalysts used herein are amines and amides, including tertiary amines in which organic groups are attached to nitrogen at its three bonds, heterocyclic tertiary organic amines and N,N-di-substituted amides. Examples are triphenylamine, tribenzylamine, trimethylamine, triethylamine, tripropylamine, tributylamine, triisobutylamine, trioctylamine, pyridine, quinoline, N,N-dimethylaniline, N-methyl-2-pyrrolidone and polyvinyl pyrrolidone. Desirable catalysts are tertiary amines such as tributylamine and N,N-dimethylaniline. Also useful are salts of tertiary amines such as tributylamine hydrochloride. It is believed that under reaction conditions, these salts are fully dissociable and release a sufficient (catalytic) amount of tertiary amines to promote the reaction.

The amount of the catalyst used is a catalytic amount and not critical. Usually, the amount of the catalyst used in the reaction system is preferably 0.1 to 2.0% by weight, especially 0.3 to 0.9% by weight based on the starting methylchlorodisilanes.

According to the invention, the reaction of methylchlorodisilanes with hydrogen chloride in the presence of the amine or amide catalyst is carried out under the condition that the amount of impurities or catalyst poisons which can deactivate the amine or amide catalyst and which are present in the disilanes and in the reaction system is less than the equimolar amount with the amine or amide catalyst.

The impurities or catalyst poisons are iron, aluminum, zinc, tin and compounds thereof.

The removal of the impurities from the high-boiling fraction is to be determined from an economical standpoint, depending on the composition of cleavable disilanes used and the reaction conditions (including a reaction temperature, a catalyst concentration, a reaction time and the ratio of reactant feed/reactor volume) used when methylchlorodisilanes are reacted with hydrogen chloride. It suffices that the removal is made such that the amount of iron, aluminum, zinc, tin and compounds thereof is less than the equimolar amount with the catalyst in the reaction system. This is because the cleavage reaction of disilanes is substantially inhibited if a more than equimolar amount of catalyst poisons (iron, aluminum, zinc, tin and compounds thereof) are present, although the degree of such inhibition varies with the reactivity of the catalyst with catalyst poisons.

As to the means for removing the impurities, it is important to use an appropriate procedure for a particular situation, with the concentration of impurities in the methylchlorodisilanes and the form and properties of impurities being taken into account. Either physical operation or chemical operation may be used as the impurity removing means. For example, when undissolvable components are to be removed by physical operation, filtration or the like is effective. When dissolvable components are to be removed, simple evaporation and flushing are applicable. In the latter case, the removal of dissolvable components may also be carried out by distillation, especially when the dissolvable impurities have a boiling point close to the cleavable methylchlorodisilanes. The conditions of unit operation should be determined by taking into account the composition of still liquid and separation specifications and optionally performing empirical confirmation. The reactor and attachments should preferably be lined with glass in order to avoid leaching of iron and compounds thereof.

Any of well-known procedures and apparatus may be employed for reacting methylchlorodisilanes with hydrogen chloride in the presence of the amine or amide catalyst in the reaction system in which the impurities are reduced or eliminated. The amount of hydrogen chloride used is preferably 1/7 to 1/3 of the amount of methylchlorodisilanes although the exact amount varies with the composition of the starting disilanes.

In the preferred embodiment of the invention, the portion of hydrogen chloride which is left unreacted in the above reaction is absorbed in a silane whereby the unreacted hydrogen chloride is fed back to the methylchlorodisilanes/hydrogen chloride reaction system for reuse.

The absorption of hydrogen chloride gas in monosilanes may use any device such as a packed column insofar as the device is one commonly used in the art. The silane used as an absorbent medium may be a monosilane such as dimethyldichlorosilane or methyltrichlorosilane in which hydrogen chloride is dissolvable. Also, the methylchlorodisilanes which are reactants herein may be used as the absorbent medium although absorption operation must be done under such conditions that the methylchlorodisilanes may not be frozen or solidified because the methylchlorodisilanes are more readily freezable than methylchlorosilanes. The absorption temperature and the amount of absorbent medium fed vary over a wide spectrum and should be determined by taking into account the amount of hydrogen chloride to be absorbed, operating conditions, economical heat balance, the investment of devices and the running cost. In general, lower temperatures are preferable because the device required for absorption may be of smaller capacity.

By the above-mentioned procedure, unreacted hydrogen chloride gas can be efficiently and economically absorbed and recovered.

As compared with prior art methods for preparing monosilanes from a high-boiling fraction formed as by-products in the direct synthesis of methylchlorosilanes by reacting the high-boiling fraction with hydrogen chloride in the presence of a catalyst, the method of the present invention has the following advantages.

(1) Since the content of impurities in the high-boiling fraction and in the reaction system is reduced before the reaction is carried out, the deactivation of the catalyst is restrained. As a result, the batch life is improved, thereby reducing the loss time of the process and the loss of silanes.

(2) Since the catalyst is not deactivated, the expense for the catalyst is minimized.

(3) By recovering unreacted hydrogen chloride for reuse, the percent utilization of the hydrogen chloride gas charge is increased. Consequently, monosilanes can be prepared in an economically advantageous manner.

(4) Since the amount of unreacted hydrogen chloride gas in the exhaust gases is reduced, the investment and running costs of a scrubbing equipment which is commonly used for the disposal of hydrogen chloride gas in the prior art are reduced.

EXAMPLE

Examples of the invention are given below by way of illustration and not by way of limitation.

Example 1 & Comparative Examples 1–4

A 1-liter glass vessel equipped with a packed column, stirrer, thermometer and inlet tube for anhydrous hydrogen chloride was used as an experimental reactor. The reactor was charged with methylchlorodisilanes and N,N-dimethylaniline catalyst. By blowing anhydrous hydrogen chloride gas into the reactor from a tank and feeding disilanes from the top of the packed column in an amount corresponding to the amount of silane product being distilled out so that the reactor level might be maintained constant, reaction was carried out under approximately atmospheric pressure. The packed column at its top was connected to a condenser and a reflux dispenser. The condenser was connected to a 500-ml glass reservoir, which was, in turn, connected to a trap in a Dewar vessel filled with methanol and solid dry ice and then to a bubble counter filled with water. Using this experimental system, experiments were made under conditions as shown in Table 1. The results are shown in Table 1.

TABLE 1

|  |  | Example | Comparative Examples | | | |
|---|---|---|---|---|---|---|
|  |  | 1 | 1 | 2 | 3 | 4 |
| Amount of methylchlorodisilanes charged (g) | Trimethyltrichlorodisilane | 308 | 295 | 310 | 427 | 327 |
|  | Dimethyltetrachlorodisilane | 612 | 371 | 390 | 601 | 411 |
|  | Other disilanes | 22 | 214 | 226 | 38 | 238 |
|  | Total | 942 | 880 | 926 | 1066 | 976 |
| Amount of disilanes fed (g) | Trimethyltrichlorodisilane | 270 | 7 | 33 | 8 | 7 |
|  | Dimethyltetrachlorodisilane | 537 | 8 | 41 | 11 | 8 |
|  | Other disilanes | 20 | 5 | 24 | 1 | 5 |
|  | Total | 827 | 20 | 98 | 20 | 20 |
| Amount of catalyst charged (g) |  | 9 | 9 | 9 | 11 | 10 |
| Amount of hydrogen chloride fed (g) |  | 157 | 100 | 83 | 47 | 55 |
| Reaction temperature (° C.) |  | 136 | 136 | 135 | 136 | 135 |
| Reaction time (hr.) |  | 5.2 | 1.8 | 2.8 | 1.6 | 1.8 |
| Additive (impurity) |  | none | Sn powder | Zn powder | Al powder | $AlCl_3$ |
| Amount of monosilanes produced (g) | Methyldichlorosilane | 372 | 0 | 0 | 0 | 0 |
|  | Trimethylchlorosilane | 22 | 0 | 0 | 0 | 0 |
|  | Methyltrichlorosilane | 301 | 0 | 0 | 0 | 0 |
|  | Dimethyldichlorosilane | 132 | 0 | 0 | 0 | 0 |
|  | Total | 827 | 0 | 0 | 0 | 0 |
| Utilization of hydrogen chloride (%) |  | 67 | 0 | 0 | 0 | 0 |

*1 The composition of continuously fed methylchlorodisilanes was the same as the composition of disilanes charged.
*2 The percent utilization of hydrogen chloride was calculated as [(amount of hydrogen chloride fed) − (amount of unreacted hydrogen chloride trapped)]/(amount of hydrogen chloride fed) × 100%.

It is evident from Table 1 that the presence of tin, zinc, aluminum, and compounds thereof obstructs the progress of reaction of methylchlorodisilanes with hydrogen chloride.

Example 2

A reactor equipped with a packed column which had been fully purged with nitrogen gas was charged with 39 kg of tributylamine and 6,400 kg of a mixture consisting of 8% of 5 tetramethyldichlorodisilane, 45% of trimethyltrichlorodisilane and 47% of dimethyltetrachlorodisilane. The mixture had an aluminum concentration of less than 1 ppm because impurities becoming catalyst poisons had been removed from the mixture by distillation.

While maintaining the reactor at a temperature of 128 to 132° C. and a pressure of 0.1 to 0.2 kg/cm²G, the mixture and hydrogen chloride gas were fed at a rate of 585 kg/hr. and 100 kg/hr., respectively, into the reactor to start reaction. The column top temperature was 58 to 62° C. To distill out of the reactor only monosilane cleavage products from the reaction, a necessary amount of reflux was maintained by the silane cleavage products. In accordance with the start of reaction, a mixture consisting of 40% of methyldichlorosilane, 34% of methyltrichlorosilane and 26% of dimethyldichlorosilane outflowed from the column head at a rate of 638 kg/hr. The exhaust gases contained unreacted hydrogen chloride gas at a rate of 3.0 kg/hr. (corresponding to an unreacted rate of 3.0%). At the point when 100 tons of the disilane mixture was processed, the unreacted hydrogen chloride gas in the exhaust gases was maintained at 3.0 kg/hr. (corresponding to an unreacted rate of 3.0%). This allowed the run to be continued.

Comparative Example 5

The procedure of Example 2 was repeated except that the disilane mixture used as reactants was a mixture consisting of 7% of tetramethyldichlorodisilane, 43% of trimethyltrichlorodisilane and 50% of dimethyltetrachlorodisilane. The mixture had an aluminum concentration of 500 ppm. In accordance with the start of reaction, a mixture of monosilanes outflowed from the column head as in Example 2. The exhaust gases contained unreacted hydrogen chloride gas at a rate of 3.0 kg/hr. (corresponding to an unreacted rate of 3.0%). At the point when 10 tons of the disilane mixture was processed, the unreacted hydrogen chloride gas in the exhaust gases increased to 30 kg/hr. (corresponding to an unreacted rate of 30.0%). Because of the low reactivity of hydrogen chloride, the run was interrupted.

Example 3

Reaction was started using the same reactants and system as in Example 2. The silanes distilling out from the column top were condensed in a condenser. Unreacted hydrogen chloride gas outflowing from the column top was led to an absorption column containing methyltrichlorosilane as an absorbent medium. The feed rate of hydrogen chloride gas was 3.0 kg/hr. when 100 tons of the disilane mixture was processed, and 2.4 kg/hr. of hydrogen chloride accounting for 80% of the feed rate was absorbed in the monosilane in the absorption column. It is noted that absorption was carried out in a packed column where hydrogen chloride was in counter-current contact with methyltrichlorosilane which was fed as the absorbent medium at a rate of 50 kg/hr. The liquid from the column bottom was circulated at a rate of about 800 kg/hr. and fed to the absorption column. The absorption temperature was about −8° C. The monosilane having hydrogen chloride absorbed therein was delivered to the reactor where the hydrogen chloride in the monosilane was used for reaction again. Owing to the absorption and recovery of unreacted hydrogen chloride by the monosilane, the utilization of the hydrogen chloride reactant was increased to 99.4%. A very compact exhaust gas disposal equipment (typically, scrubber) was fully effective for preventing the hydrogen chloride gas from being released to the air.

Comparative Example 6

The hydrogen chloride gas given off as in Example 3 was treated by means of a scrubber in which the exhaust gases were scrubbed with water as the absorbent medium, instead of the absorption column using a monosilane as the absorbent medium. The utilization of the hydrogen chloride reactant was 97%. The scrubber as the exhaust gas disposal equipment was of a greater size than the scrubber used in Example 3 and required a greater investment. A greater load was imposed on an equipment for the disposal of hydrogen chloride in discharge water.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for preparing monosilanes from a high-boiling fraction formed as by-products in the direct synthesis of methylchlorosilanes to react metallic silicon with methyl chloride in the presence of a copper catalyst, the high-boiling fraction consisting essentially of methylchlorodisilanes of the general formula (1):

$$(CH_3)_a Si_2 Cl_{6-a} \tag{1}$$

wherein letter a is an integer of 2 to 6, said method comprising the step of reacting the high-boiling fraction with respect to hydrogen chloride in the presence of an amine or amide catalyst under the condition that the amount of iron, aluminum, zinc, tin and compounds thereof present in the reaction system is less than the equimolar amount with the catalyst.

2. The method of claim 1 further comprising the step of reducing the concentration of iron, aluminum, zinc, tin and compounds thereof in the high-boiling fraction before the high-boiling fraction is subject to the reaction step.

3. The method of claim 2 wherein the step of reducing the concentration of iron, aluminum, zinc, tin and compounds thereof in the high-boiling fraction is carried out by distillation.

4. The method of claim 1 wherein said amine or amide catalyst is a tertiary amine or N,N-dimethylaniline.

5. The method of claim 1 further comprising the steps of causing a silane to absorb unreacted hydrogen chloride and recycling the hydrogen chloride-absorbed silane to the reaction system of said high-boiling fraction and hydrogen chloride.

6. The method of claim 1, wherein the reaction of the high-boiling fraction with hydrogen chloride is conducted in a lined reactor.

7. The method of claim 2, wherein the concentration of aluminum chloride in the high-boiling fraction is reduced before the reaction step.

8. The method of claim 1, wherein the catalyst is triphenylamine, tribenzylamine, trimethylamine, triethylamine, tripropylamine, tributylamine, triisobutylamine, trioctylamine, pyridine, quinoline, N,N-dimethylaniline, N-methyl-2-pyrrolidone, polyvinyl pyrrolidone or tributylamine hydrochloride.

9. The method of claim 1, wherein the amount of the catalyst used is from 0.1 to 2.0% by weight based on the starting methylchlorodisilanes.

10. The method of claim 1, wherein the amount of hydrogen chloride is 1/7 to 1/5 of the amount of methylchlorodisilanes.

* * * * *